Figure 1:
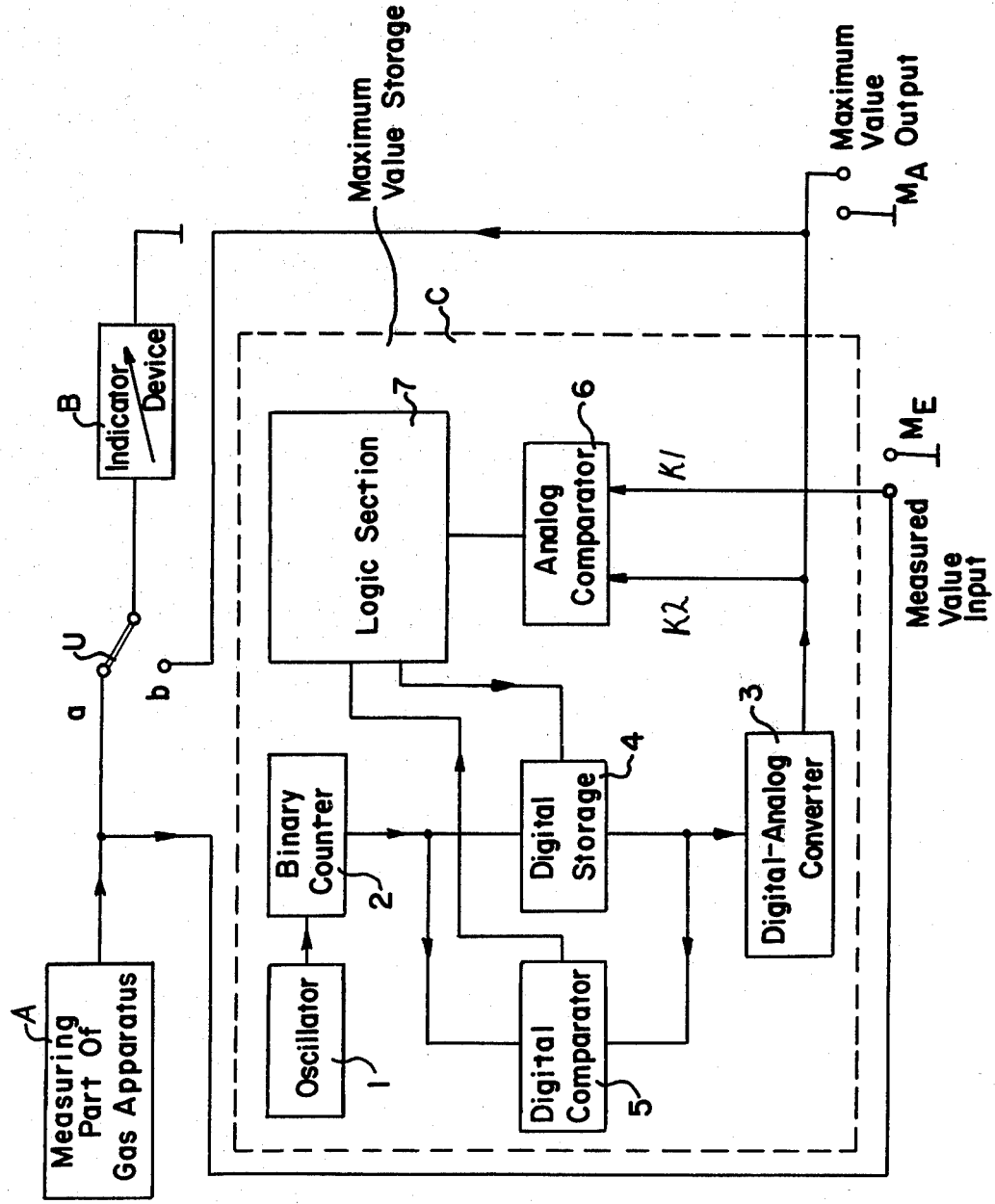

United States Patent [19]

Fengler

[11] 4,393,686
[45] Jul. 19, 1983

[54] CIRCUIT ARRANGEMENT FOR A GAS MEASURING AND GAS ANALYSIS APPARATUS

[75] Inventor: Hans-Jörg Fengler, Berlin, Fed. Rep. of Germany

[73] Assignee: Auergesellschaft GmbH, Berlin, Fed. Rep. of Germany

[21] Appl. No.: 298,015

[22] Filed: Aug. 31, 1981

[30] Foreign Application Priority Data

Aug. 21, 1980 [DE] Fed. Rep. of Germany ....... 3031555

[51] Int. Cl.³ .......................................... G01N 31/00
[52] U.S. Cl. ........................................ 73/23; 340/632
[58] Field of Search ................ 73/23, 27 R; 340/632, 340/633, 634; 422/98

[56] References Cited

U.S. PATENT DOCUMENTS 4,064,498 12/1977 Burr et al. ........................... 340/632

Primary Examiner—Stephen A. Kreitman
Attorney, Agent, or Firm—Carothers & Carothers

[57] ABSTRACT

A circuit arrangement for an apparatus for measuring and analyzing gases which emits a signal when a specified gas concentration is exceeded and which is capable of recalling the maximum value of gas concentration measured. A binary counter acted upon by an oscillator is connected to a digital-analog converter via a digital storage, and a digital-comparator compares the binary values of the counter output from the binary counter and the input to the digital-analog converter. An analog comparator receives the measured value input from a gas measuring device and the maximum value output from the digital-analog converter, and the digital storage is opened via a logic section when the voltage at the measured value input is greater than the voltage at the maximum value output and the digital storage also has equal signals at the input and output thereof.

5 Claims, 2 Drawing Figures

CIRCUIT ARRANGEMENT FOR A GAS MEASURING AND GAS ANALYSIS APPARATUS

The invention concerns a circuit arrangement for a gas measuring and gas analysis apparatus.

Known types of gas measuring and gas analysis devices release an optical or acoustical alarm when a specified gas concentration is exceeded. However, in such cases, the maximum value of the gas concentration can only be read once, and, in fact, only when immediately observing the indicating device. Since, after a short period of time, the value of the gas concentration can decrease again, a true measurement is not always possible. Another drawback that can reveal itself in the event of an accident, such as one occurring under ground, is that the decisive measured value leading to the accident can no longer be determined after the event, even though the gas measuring apparatus is undamaged.

The basic object of the invention is to create a circuit arrangement with the lowest technological expenditure in order to be able, at any time, to reproduce or recall the maximum value of the gas concentration measured by the gas measuring and gas analyzing apparatus.

This object is accomplished in accordance with the invention by the features presented in the appended claims.

The advantages to be gained by the invention reside, in particular, in the fact that the measured-value storage, made in accordance with the invention, makes it unnecessary to carry out a concentrated and continuous reading of the indicating device in a gas measuring and gas analyzing apparatus in order, for example, to be able to determine the often decisive maximum measured value of a gas concentration. This is especially advantageous in the indicating device of a gas measuring apparatus with a ballistic indication behavior, whereby the measured value briefly attains a maximum, only to drop again after the combustion. The reading of the indicating device is simplified by the incorporation of the measured-value storage since, after the measuring phase, it is required only to read the maximum value.

Figure 2:
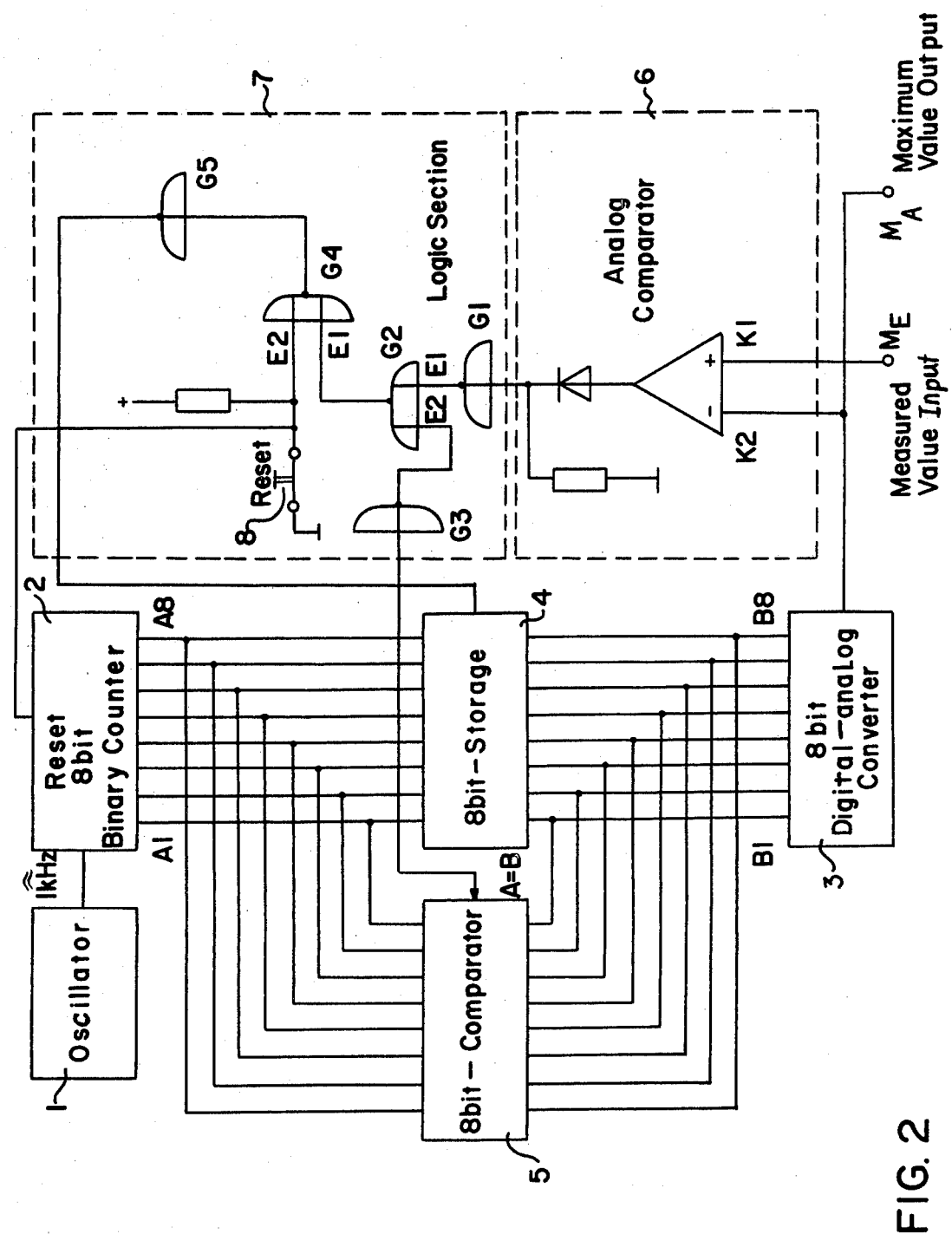

An embodiment of the invention is illustrated by way of example in the appended drawings and described in detail in the following, in which FIG. 1 presents a circuit arrangement in the form of a block diagram of the gas measuring and gas analyzing apparatus made in accordance with the invention with a maximum-value storage; and FIG. 2 is a schematic diagram which illustrates, by way of example, an embodiment of the invention.

As may be seen from FIG. 1, the circuit arrangement for reproducing and indicating, at any time, at the indicating device B, the maximum value of the gas concentration measured by the measuring part (or sensor) A of the gas measuring apparatus, consists of the maximum-value storage C, which is connected between the said measuring part A and the indicating device B and which consists of a digital and an analog circuit part.

A free-running oscillator 1 continuously pulses, at a high frequency, a binary counter 2 which is separated from a digital-analog converter 3 by a digital storage 4. A digital comparator 5 compares the binary values of the counter outputs from the binary counter 2 with the inputs to the digital-analog converter 3.

An analog comparator 6 is connected to the input $K_1$ with the measured value input $M_E$ coming from the measuring part A, and to the input $K_2$ with the maximum value output of the digital-analog converter 3.

The analog comparator 6 actuates a digital logic section 7 which, in essence, consists of a logical connection of NOR gates which open or close the digital storage 4.

By actuating a chargeover switch U from the setting a to b, the maximum gas concentration stored in the maximum value storage C can be made indicatable on the indicating device B.

In the following, a description is given of the mode of operation of the circuit arrangement illustrated in FIG. 2.

When the voltage at the measured value input $M_E$ exceeds the stored maximum value $M_A$, coming from the digital-analog converter 3 at the output of the converter, the analog comparator 6 then becomes positive or it switches over and the higher potential "H", that is the binary allocation "High Level", lies at the input of the NOR-gate $G_1$.

The input $E_1$ of the NOR gate $G_2$ is primed with the lower potential "L", that is, with the binary "Low Level" allocation. In other words, the NOR gate $G_1$ inverts the positive signal from the analog comparator 6. At the moment the digital comparator 5 detects that the binary 8-bit information values of the input and output of the digital storage 4 correspond and are equal, the NOR gate $G_2$ becomes activated in that the output signal from the digital comparator 5 is delivered with the binary allocation 1 via the NOR gate $G_3$ to the input $E_2$ of the NOR gate $G_2$. The input $E_1$ of the NOR gate $G_4$ is charged with the higher potential "H" and opens the digital storage 4 via the NOR gate $G_5$. By this means, there is attained a true "forward thrust" of the momentary maximum value. From this moment on, the contents of the counter or the counter information of binary counter 2 are passed directly on to the analog converter 3 which increases its output voltage until such time that the voltage of the measured-value input $M_E$ is reached. The digital storage 4 is then immediately closed via the gate connection of the logic section 7, since the input to the NOR gate $G_1$ becomes "L", and the gates $G_1$, $G_2$, $G_4$ and $G_5$ change their logic states.

The last binary information to be stored during the switch-over phase is yielded by the blocked digital storage 4 to the digital analog converter 3. The converted analog value can be measured at all times at the output of the converter 3. The above-described process is caused to begin anew as soon as this value is exceeded at the measured-value input $M_E$ of the indicating device.

In order to be able to unequivocally determine the momentary maximum measured-value of an arbitrary point of the measuring range, it is advantageous to set the binary counter to zero by actuating a reset key 8 in order to bring the measured-value output $M_A$ to the level of the measured-value input $M_E$, even when the latter has smaller values.

According to the provisions of the patent statutes, I have explained the principle of my invention and have illustrated and described what I now consider to represent its best embodiment. However, I desire to have it understood that, within the scope of the appended claims, the invention may be practiced otherwise than as specifically illustrated and described.

I claim:

1. A circuit arrangement for an apparatus for measuring and analyzing gases and consisting of a measuring part with an indicating and warning device, characterized by the provision of:

(a) a binary counter which is acted upon by an oscillator and which is connected to a digital-analog converter through a digital storage,
(b) a digital-comparator connected for comparing the binary values of the counter output from the binary counter and the input to the digital-analog converter,
(c) an analog comparator which is connected to a measured-value input from the measuring part and to a maximum value output of the digital-analog converter, the analog comparator connected to a digital section and adapted for actuating the digital logic section such that said logic section opens and closes the digital storage, and
(d) a chargeover switch located between the measuring part and the indicating device and connected for switching the maximum value output to the measured value input on the input of said indicating device.

2. A circuit arrangement in accordance with claim 1, characterized in that the digital-comparator forms a connecting link between the digital and analog portions of the circuit, and constitutes an AND-linkage with the digital-analog converter.

3. A circuit arrangement in accordance with claim 1, characterized in that said analog comparator is adapted to open the digital storage via the logic section when the voltage at the measured-value input is greater than the voltage at the maximum value output and when the digital storage has equal signals at the input and the output thereof.

4. A circuit arrangement in accordance with claim 1, characterized in that the digital logic section is a logic linkage consisting of NOR gates.

5. A circuit arrangement in accordance with claim 1, characterized in that a reset key is provided in the logic section which is connected to bring the binary counter to zero when actuated so that the measured-value output can be adjusted to the level of the measured-value input.

* * * * *